US007787121B2

(12) United States Patent
Tsujita et al.

(10) Patent No.: US 7,787,121 B2
(45) Date of Patent: Aug. 31, 2010

(54) IMAGING APPARATUS (75) Inventors: Kazuhiro Tsujita, Ashigarakami-gun (JP); Hiroshi Sunagawa, Ashigarakami-gun (JP); Katsuya Kikuchi, Saitama (JP); Tetsuya Kawanishi, Saitama (JP)

(73) Assignees: FUJIFILM Corporation, Tokyo (JP); Fujinon Corporation, Saitama-ken (JP)

( * ) Notice: Subject to any disclaimer, the term of this patent is extended or adjusted under 35 U.S.C. 154(b) by 228 days.

(21) Appl. No.: 12/175,033

(22) Filed: Jul. 17, 2008

(65) Prior Publication Data

US 2009/0021739 A1    Jan. 22, 2009

(30) Foreign Application Priority Data

Jul. 18, 2007    (JP)    ............................. 2007-187170
May 27, 2008    (JP)    ............................. 2008-137372

(51) Int. Cl.
    *G01N 21/25*    (2006.01)
(52) U.S. Cl. ...................................... 356/407
(58) Field of Classification Search ................. None
    See application file for complete search history.

(56) References Cited

U.S. PATENT DOCUMENTS

| 4,717,952 A | | 1/1988 | Kohayakawa et al. |
| 5,223,715 A | * | 6/1993 | Taylor ........................ 250/343 |
| 5,255,087 A | | 10/1993 | Nakamura et al. |
| 5,879,284 A | | 3/1999 | Tsujita |
| 2003/0007254 A1 | * | 1/2003 | Tocci ......................... 359/663 |
| 2005/0027166 A1 | | 2/2005 | Matsumoto et al. |
| 2006/0071156 A1 | | 4/2006 | Masaki |

FOREIGN PATENT DOCUMENTS

| JP | 10-165365 A | 6/1998 |
| JP | 2003-093336 A | 4/2003 |
| JP | 2006-337399 A | 12/2006 |
| WO | 2006/129872 A1 | 12/2006 |

OTHER PUBLICATIONS

Yoichi Miyake, "Analysis and Evaluation of Digital Color Image," University of Tokyo Press, 2000, p. 148-153 and partial translation thereof.

* cited by examiner

*Primary Examiner*—Tu T Nguyen
(74) *Attorney, Agent, or Firm*—Sughrue Mion, PLLC (57) ABSTRACT

An imaging apparatus includes a light source unit that selectively outputs white light and light in a different wavelength band to an observation target, an imaging unit including an imaging device, and a spectral image formation circuit that generates a spectral image signal for a specified wavelength by an operation using an image signal based on an output from the imaging unit and predetermined matrix data. The imaging unit selectively obtains an image of the observation target for each of first, second and third light components in a visible light region and an image for each of at least fourth and fifth light components in a near-infrared region. Further, the imaging unit includes first spectral devices that make only the first and fourth light components enter first pixels of the imaging device and second spectral devices that make only the second and fifth light components enter second pixels thereof.

6 Claims, 8 Drawing Sheets

IMAGING APPARATUS

BACKGROUND OF THE INVENTION

1. Field of the Invention

The present invention relates to an imaging apparatus, and more specifically to an imaging apparatus that forms a spectral image (spectroscopic image) in a predetermined wavelength range (band) by performing operation processing on an image signal that is obtained by imaging an object to be observed (an observation target) that is illuminated with light.

2. Description of the Related Art

In recent years, in the field of imaging apparatuses, such as electronic endoscopes using solid-state imaging devices, imaging apparatuses that perform spectral imaging (spectroscopic imaging) by using narrow band-pass filters in combination have drawn attention. These imaging apparatuses (Narrow Band Imaging—NBI) have built-in narrow band-pass filters and the combination of the narrow band-pass filters is determined based on the spectral reflectance at digestive organs (gastric mucosa or the like). The imaging apparatus includes three narrow band-pass filters, which pass light in narrow (wavelength) bands, instead of a field-sequential-type (frame-sequential-type) rotation filter of R (red), G (green) and B (blue). In the imaging apparatus with the built-in narrow band filters, illumination light is sequentially output through the three narrow band-pass filters to illuminate an observation target, thereby obtaining three signals. Further, the obtained signals are processed in a manner similar to the processing performed in the case of R, G and B signals (RGB signals), while the degree of weighting is changed for each of the three signals. Accordingly, a spectral image is formed. If such a spectral image is used, it is possible to extract microstructures or the like from images of digestive organs, such as a stomach or large intestine, which could not be detected in the conventional method.

Besides the field-sequential-type endoscope using the narrow band-pass filters, a simultaneous-type endoscope that forms a spectral image by performing operation processing has been proposed. In the simultaneous-type endoscope, micromosaic color filters are arranged on a solid-state imaging device and the spectral image is formed by performing operation processing based on image signals obtained by using white light, as disclosed in Japanese Unexamined Patent Publication No. 2003-093336 and Yoichi Miyake, "Analysis and Evaluation of Digital Color Image", University of Tokyo Press, 2000, pp. 148-153. In this method, the relationship between numerical data representing the color sensitivity characteristic for each of R, G and B and numerical data representing the spectral characteristic of a specific narrow band-pass filter is obtained as matrix data (a set of coefficients). Further, an operation is performed by using the matrix data and R, G and B signals. Accordingly, a spectral image signal representing an estimated spectral image that will be obtained by passing light through the narrow band-pass filter is obtained. If the spectral image is formed through such operations, it is not necessary to prepare a plurality of filters corresponding to desirable wavelength ranges. Further, it is not necessary to change the arrangement of the filters. Therefore, it is possible to prevent the size of the apparatus from becoming large. Further, it is possible to reduce the cost of the apparatus.

Meanwhile, in the field of observation of living organisms (organisms, living bodies or the like), as described above, a technique of observing fluorescence images of blood vessels, cancer cells or the like by marking them with a fluorescent marker (a fluorescent agent, a fluorescent reagent or the like) is used. Further, when such technique is used, application of the aforementioned spectral image technique to obtainment of the fluorescence images is considered. In observation of the living organisms, when absorption of light by water and hemoglobin contained in the living organisms is taken into consideration, it is desirable that the wavelength of the fluorescence and the wavelength of excitation light are approximately in the range of 600 to 1300 nm, and optionally in the range of 700 to 1300 nm, which is a near-infrared region.

However, the aforementioned apparatus, which obtains spectral images by performing operation processing, obtains spectral images in a visible light region by using R, G and B signals for ordinary images (color images). In other words, the apparatus is not designed to cope with the aforementioned wavelength ranges, i.e., 600 to 1300 nm and 700 to 1300 nm. Therefore, an additional optical system is needed to obtain a spectral image in the aforementioned wavelength range in addition to an ordinary image. Hence, there are problems that the size of the apparatus becomes large and that the cost significantly increases.

SUMMARY OF THE INVENTION

In view of the foregoing circumstances, it is an object of the present invention to provide an imaging apparatus that can form spectral images in a near-infrared region in addition to ordinary images without increasing the size of the apparatus and without significantly increasing the cost of the apparatus.

An imaging apparatus according to the present invention is an imaging apparatus comprising:

a light source unit that can selectively output white light and light in a wavelength band that is different from that of the white light to an observation target;

an imaging unit that includes an imaging device for imaging the observation target that is illuminated with the light output from the light source unit, the imaging device having first pixels and second pixels, and the imaging unit further including first spectral devices that make only first light components in a visible light region and fourth light components in a near-infrared region enter the first pixels of the imaging device and second spectral devices that make only second light components in the visible light region and fifth light components in the near-infrared region enter the second pixels of the imaging device, wherein the imaging unit selectively obtains an image of the observation target for each of the first light components, the second light components and third light components, which are three kinds of light components in different wavelength ranges from each other in the visible light region, and an image of the observation target for each of at least the fourth light components and the fifth light components, which are at least two kinds of light components in different wavelength ranges from each other in the near-infrared region; and a spectral image formation circuit that generates a spectral image signal representing a spectral image that has a specified wavelength by performing an operation using an image signal based on an output from the imaging unit and predetermined matrix data.

Here, the "light in a wavelength band that is different from that of the white light" should be light in a wavelength band, the entire range of which is not exactly the same as that of the white light. In other words, the wavelength band of the light may overlap with that of the white light. For example, light in the range of red to near-infrared region may be used as the "light in a wavelength band that is different from that of the white light". Further, in the expression "the first light components, the second light components and third light components, which are three kinds of light components in different wavelength ranges from each other" and in the expression "at least the fourth light components and the fifth light components, which are at least two kinds of light components in different wavelength ranges from each other", the phrase "in different wavelength ranges from each other" means that the entire ranges of these different kinds of light components should not be exactly the same. In other words, the wavelength bands may overlap with each other.

In the expression "can selectively output . . . to an observation target" and the phrase "selectively obtaining an image", the term "selectively" means that the operation may be performed in time division (in other words, by temporally dividing the operation in such a manner that the operations are performed at different time from each other), for example.

Further, in the specification of the present application, the short-wavelength-side boundary value of the "near-infrared region" is approximately 700 nm.

Meanwhile, the phrase "only first light components . . . and fourth light components . . . " and the phrase "only second light components . . . and fifth light components . . . " refer to only the light components within the wavelength bands of light output from the light source unit. In other words, with regard to other wavelength bands, the light components are not limited to the light components mentioned in the phrases.

In the imaging apparatus, it is desirable that the spectral image formation circuit generates the spectral image signal by using the image signal that is at least based on the fourth light components and the fifth light components.

In the imaging apparatus, the specified wavelength may be the wavelength of fluorescence and the light in a wavelength band that is different from that of the white light may be excitation light for exciting the fluorescence.

Further, it is desirable that the imaging apparatus can form a color image based on the first light components, the second light components and the third light components in the visible light region, a first spectral image based on at least two of the first light components, the second light components and the third light components in the visible light region and a second spectral image based on at least the fourth light components and the fifth light components in the near-infrared region.

In that case, it is desirable that at least two of the color image, the first spectral image and the second spectral image can be displayed at the same time.

Further, it is desirable that at least two of the color image, the first spectral image and the second spectral image can be displayed in such a manner that they are superimposed one on another.

In the imaging apparatus of the present invention, the imaging unit can obtain an image of an observation target for each of at least the fourth light components and the fifth light components, at least two kinds of light components in different wavelength bands from each other in a near-infrared region. Further, the spectral image formation circuit can generate a spectral image signal in the near-infrared region. Therefore, it is possible to form a spectral image in the near-infrared region. Further, the light source unit can selectively output white light and light in a wavelength band that is different from that of the white light. Further, the first pixels can receive the first light components and the fourth light components by the first spectral devices, and the second pixels can receive the second light components and the fifth light components by the second spectral devices. Therefore, it is possible to perform imaging for the visible light region and imaging for the near-infrared region by using the same imaging device by temporally dividing the imaging operation (at different time from each other). Therefore, it is not necessary to separately provide an optical system for the visible light region and an optical system for the near-infrared region. Hence, it is possible to obtain ordinary images and spectral images in the near-infrared region without increasing the size of the apparatus and without significantly increasing the cost of the apparatus.

DESCRIPTION OF THE PREFERRED EMBODIMENTS

Figure 1:
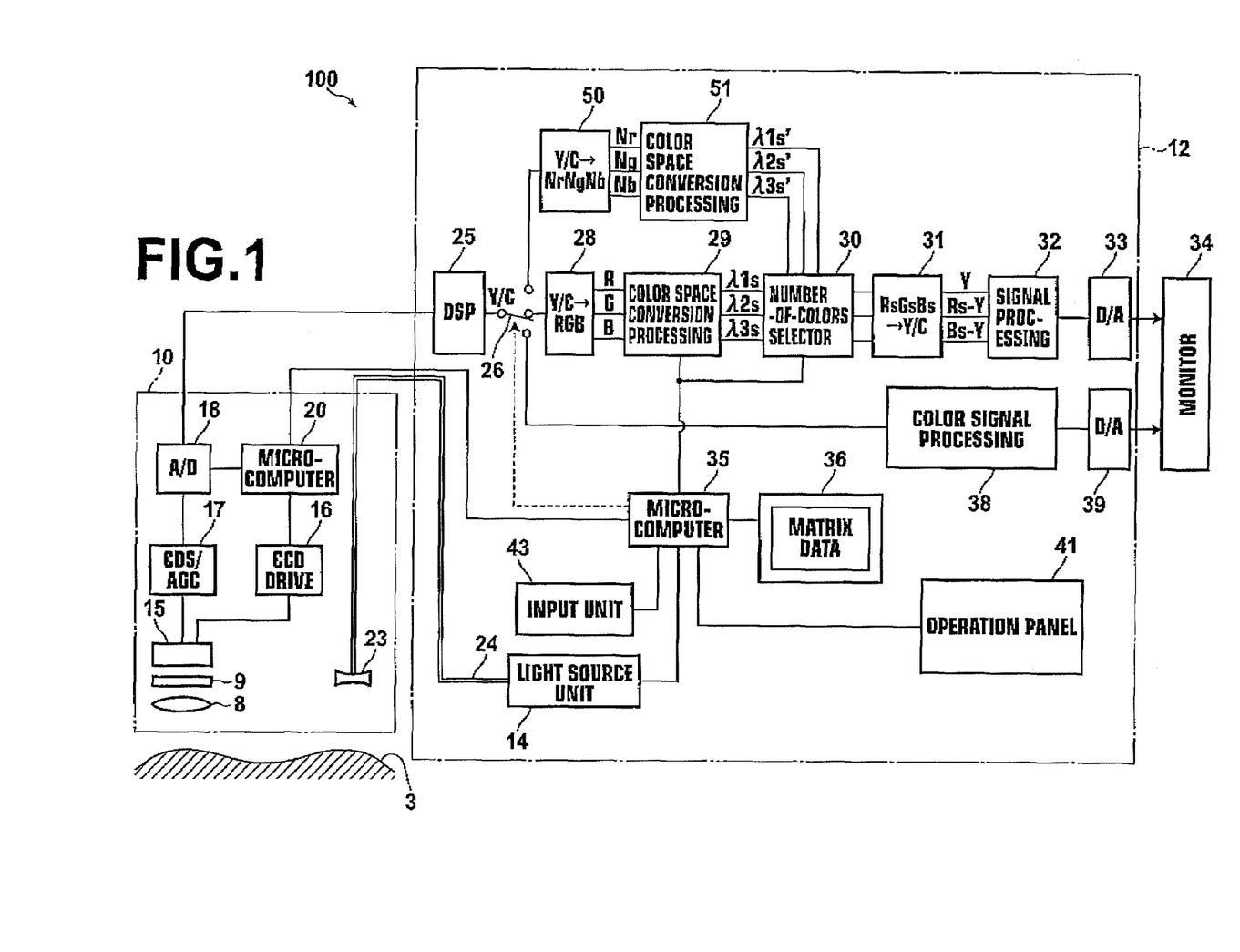
FIG. 1 is block diagram illustrating the configuration of an electronic endoscope apparatus according to a first embodiment of the present invention.

Hereinafter, embodiments of the present invention will be described in detail with reference to the attached drawings. FIG. 1 is a block diagram illustrating an electronic endoscope apparatus 100, as an imaging apparatus according to a first embodiment of the present invention. The electronic endoscope apparatus 100 according to the present embodiment operates in an ordinary image mode and in a spectral image mode. In the ordinary image mode, an ordinary image of an observation target is formed. In the spectral image mode, a spectral image of the observation target is displayed. The spectral image is obtained by performing operation processing that will be described later. Further, under the spectral image mode, the electronic endoscope apparatus 100 operates in a visible spectral image mode and in a near-infrared spectral image mode. In the visible spectral image mode, a spectral image in a visible light region is formed based on image signals (R, G and B signals) of three colors in the visible light region. In the near-infrared spectral image mode, a spectral image in a near-infrared region is formed based on image signals (Nr, Ng and Nb signals, which will be described later) of three colors in the near-infrared region.

As illustrated in FIG. 1, the electronic endoscope apparatus 100 basically includes a scope 10 for observing an observation target 3 (an object 3 to be observed) and a processor apparatus 12 to which the scope 10 is detachably connected. Further, a light source unit 14 for outputting light to the observation target 3 is provided in the processor apparatus 12. Further, at the leading end of the scope 10, an optical system 23 for illumination is provided. The optical system 23 for illumination faces an end of a light guide 24. The other end of the light guide 24 is connected to the light source unit 14. The light source unit 14 may be arranged in a light source apparatus that is separate from the processor apparatus 12.

Figure 2:
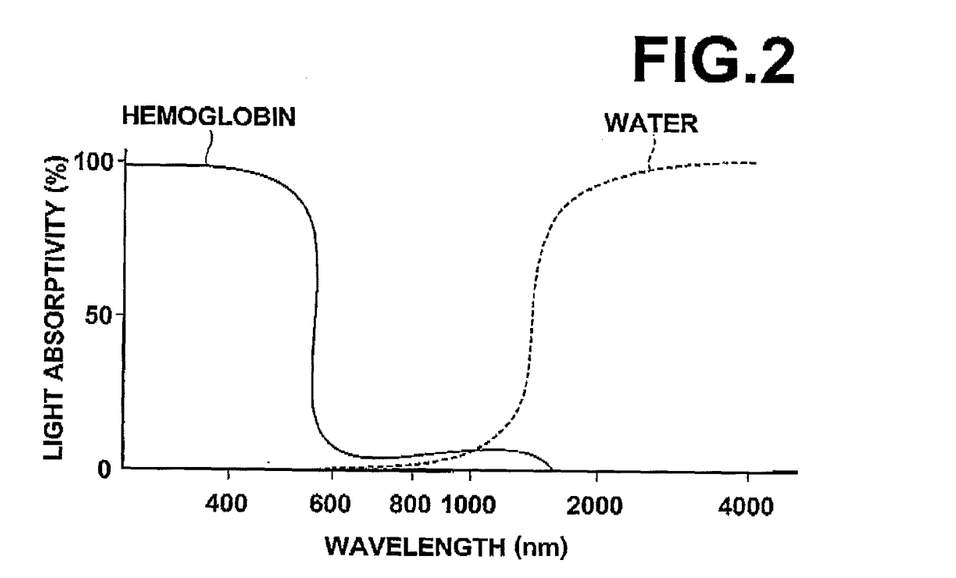
FIG. 2 is a diagram illustrating the wavelength characteristic of the light absorptivity of water and that of hemoglobin.

In the present embodiment, the observation target 3 is a living organism tissue (living body tissue) in the body cavity of the organism. The observation target 3 is marked with three kinds of fluorescent agents (reagents, markers or the like) for different wavelengths from each other. FIG. 2 illustrates the wavelength band of light that is absorbed by each of water and hemoglobin, which are contained in the living organism tissue in large amounts. As illustrated in FIG. 2, absorption by hemoglobin occurs in the wavelength band on the short wavelength side and absorption by water occurs in the wavelength band on the long wavelength side. Therefore, it is recognized that light in a wavelength range of 600 to 1300 nm, in other words, red-to-near-infrared light passes through the living organism tissue relatively well. Hence, in the present embodiment, fluorescent agents, the wavelengths of the excitation light of which are in the range of 600 to 1300 nm, are selected.

As such fluorescent agents, DyLight680, Cy7 and ICG (indocyanine green) may be used, for example. DyLight680 is a fluorescent agent that has an excitation-light wavelength of 682 nm and a fluorescence wavelength of 715 nm. Cy7 is a fluorescent agent that has an excitation-light wavelength of 747 nm and a fluorescence wavelength of 776 nm. ICG is a fluorescent agent that has an excitation-light wavelength of 785 nm and a fluorescence wavelength of 805 nm.

A plurality of fluorescent agents that are used in examination may mark different tissues from each other. Alternatively, the plurality of fluorescent agents may mark the same tissue. For example, if a plurality of kinds of fluorescent agents that can mark cancer tissue are used at the same time, the accuracy in detection of cancers can be improved, thereby increasing the rate of correct diagnosis.

Figure 3:
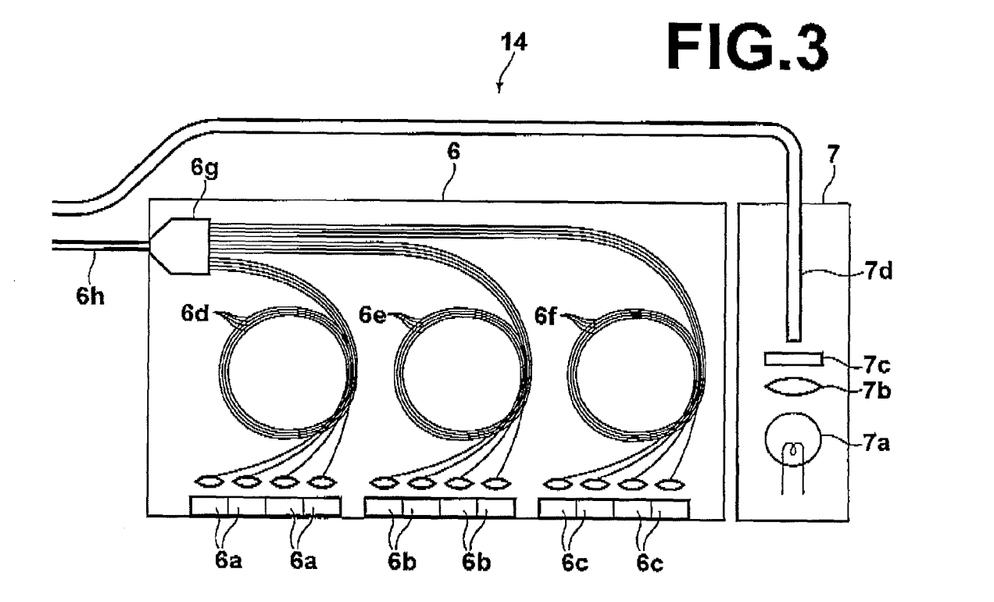
FIG. 3 is a diagram illustrating the structure of a light source unit.

FIG. 3 is a diagram illustrating an example of the structure of the light source unit 14. As illustrated in FIG. 3, the light source unit 14 includes an excitation light source unit 6 for outputting light in a red-to-near-infrared region and a white light source unit 7 for outputting white light. The light source unit 14 can selectively output the white light and the red-to-near-infrared light to the objection target 3. Specifically, in the present embodiment, the white light and the red-to-near-infrared light may be output to the observation target 3 at different time from each other (by temporally dividing the output of light). The excitation light source unit 6 outputs excitation light for exciting the fluorescent agent with which the observation target 3 has been marked. The excitation light source unit 6 is used when the electronic endoscope apparatus 100 operates in the near-infrared spectral image mode. In the present embodiment, the white light source unit 7 outputs white light only within the visible light region. The white light source unit 7 is used when the electronic endoscope apparatus 100 operates in the ordinary image mode and in the visible spectral image mode.

The excitation light source unit 6, illustrated in FIG. 3, includes a multiplicity of light sources 6a, 6b and 6c and a multiplicity of multimode optical fibers 6d, 6e and 6f. The light sources 6a, 6b and 6c output excitation light for exciting three kinds of fluorescent agents, the excitation light having wavelengths different from each other. The light output from the light sources 6a, 6b and 6c enter the multimode optical fibers 6d, 6e and 6f, respectively.

As the light sources 6a, 6b and 6c, a semiconductor laser, high-brightness LED (light-emitting diode), xenon flash lamp or the like may be used. It is desirable that each of the light sources 6a, 6b and 6c outputs narrow-band light that has a half width of approximately ±10 nm or less with respect to the center wavelength thereof. When light sources that output narrow-band light are not used as the light sources 6a, 6b and 6c, a narrow band-pass filter that transmits light in a narrow band, light having a half width of approximately ±10 nm, may optionally be provided in the light path between each of the light sources 6a, 6b and 6c and the observation target 3.

At a light incident end of each of the optical fibers 6d, 6e and 6f, a lens is monolithically formed by processing the end thereof. Therefore, it is possible to efficiently couple the light emitted from the light sources 6a, 6b and 6c to the optical fibers 6d, 6e and 6f. In the present embodiment, the optical fibers 6d, 6e and 6f, in which the lenses are monolithically formed, are used to reduce the number of parts included in the electronic endoscope apparatus 100. Alternatively, ordinary optical fibers, in which lenses are not monolithically formed, and lenses for coupling light into the optical fibers may be used.

In FIG. 3, four light sources and four optical fibers are illustrated to simplify the drawing. However, an actual electronic endoscope apparatus includes a multiplicity of light sources and a multiplicity of optical fibers. The number of the light sources and that of the optical fibers may be the same. Alternatively, the numbers may be different from each other. Further, light emitted from a single light source may enter a plurality of optical fibers.

All of the light emission ends of the optical fibers 6d, 6e and 6f are connected to an end of a coupler (wave combiner) 6g. Further, the other end of the coupler 6g is connected an optical fiber 6h that has a small diameter. The light output from the light sources 6a, 6b and 6c propagates through the optical fibers 6d, 6e and 6f. Then, the light is combined by the coupler 6g and transmitted through the optical fiber 6h.

As the coupler 6g, an optical coupler or the like may be used, for example. Alternatively, instead of using the coupler 6g, the cores of the optical fibers at the light emission ends thereof may be combined (integrated) with each other. Further, when light emitted from a multiplicity of light sources is combined by using the optical fibers, as described above, the technique disclosed in Japanese Unexamined Patent Publication No. 2006-337399 may be adopted, for example.

If the excitation light source unit 6, which is structured as described above, is used, it is possible to transmit light emitted from a multiplicity of light sources through an optical fiber that has a small diameter. Therefore, it is possible to obtain light that has high brightness and a high output level (intensity).

In the aforementioned example, three fluorescent agents are used. Therefore, the excitation light source unit 6 includes three kinds of light sources for obtaining excitation light that is most appropriate for each of the fluorescent agents. However, if a plurality of fluorescent agents can be excited by one kind of excitation light, the number of the kinds of the light sources may be less than three. Alternatively, the excitation light source unit 6 may include four or more kinds of light sources for excitation to excite various kinds of fluorescent agents.

Meanwhile, the white light source unit 7 includes a white light source 7a for outputting white light, a lens 7b for coupling light, a filter 7c and an optical fiber 7d. The filter 7c transmits light only in the visible light region. Further, the light output from the white light source 7a is condensed by the lens 7b and enters the optical fiber 7d. The optical fiber 7d and the optical fiber 6h form a light guide 24.

In the present embodiment, the filter 7c is provided within the light source unit 14. Alternatively, the filter 7c may be removably provided in the optical path between the light source unit 14 and the observation target 3. Then, the filter 7c may be inserted into the optical path when the electronic endoscope apparatus 100 operates in the ordinary image mode and in the visible spectral image mode. The filter 7c may be removed from the optical path when the electronic endoscope apparatus 100 operates in the near-infrared spectral image mode. Further, instead of providing the filter 7c within the light source unit 14, a near-infrared light cut filter may be removably provided in the optical path between the observation target 3 and a CCD sensor 15. The near-infrared light cut filter cuts near-infrared light and light that has a longer wavelength than the near-infrared light. The near-infrared light cut filter may be inserted into the optical path in the ordinary image mode and in the visible spectral image mode. The near-infrared light cut filter may be removed from the optical path in the near-infrared spectral image mode.

At the leading end of the scope 10 illustrated in FIG. 1, an imaging lens (image formation lens) 8, an excitation light cut filter 9 and the CCD (charge coupled device) sensor 15 are coaxially arranged in this order. The imaging lens 8 forms an image of the observation target 3 on the CCD sensor 15. As the excitation light cut filter 9, a notch filter may be used, for example, so that only the excitation light is blocked and the fluorescence is transmitted. The notch filter blocks light only in an extremely narrow band.

Figure 4A:
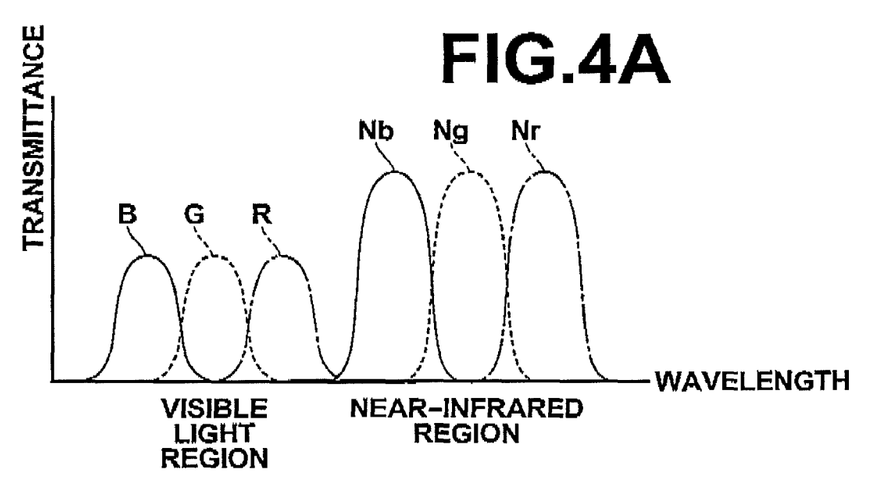
FIG. 4A is a diagram illustrating the spectral transmission characteristics of color filters.

The CCD sensor 15 constitutes an imaging unit for imaging the observation target 3 that is illuminated with light output from the light source unit 14. The CCD sensor 15 has a function for outputting image signals, as R (red), G (green) and B (blue) signals, by dividing light into three primary color components of R, G and B in the visible light region and by imaging the observation target 3 for each of the color components. Further, the CCD sensor 15 has a function for outputting image signals, as Nr, Ng and Nb signals, by dividing light into three color components of Nr, Ng and Nb in the near-infrared region and by imaging the observation target 3 for each of the color components. As illustrated in FIG. 4A, the color components Nb, Ng and Nr have wavelength bands that have a predetermined wavelength band width and are set in this order from the short-wavelength side in the near-infrared region. For example, Nb, Ng and Nr may be regarded as pseudo-three-primary-colors in the near-infrared region, which correspond to ordinary three primary colors.

Figure 4B:
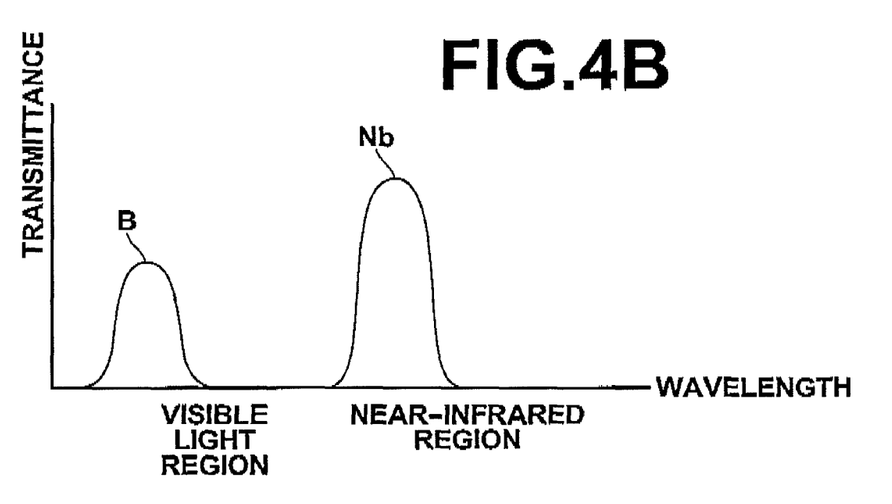
FIG. 4B is a diagram illustrating the spectral transmission characteristics of color filters.
Figure 5:
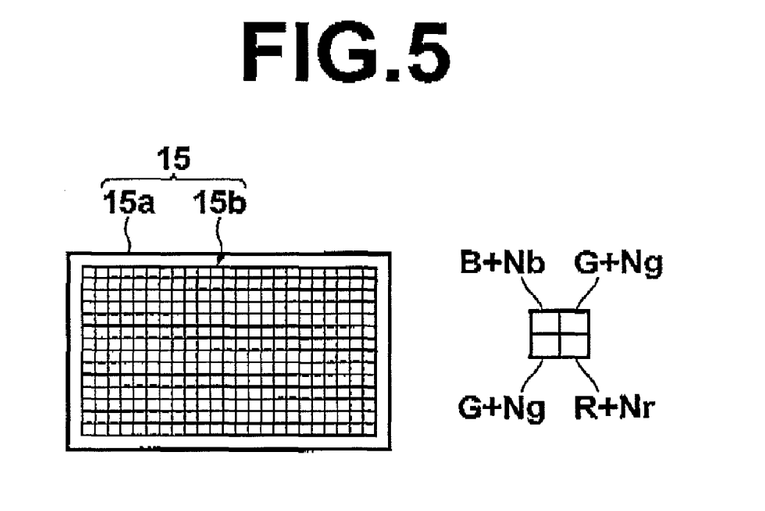
FIG. 5 is diagram illustrating the structure of one of examples of an imaging unit.

FIG. 5 is a diagram illustrating the structure of an example of the CCD sensor 15, which has the aforementioned function. In the left side of FIG. 5, the whole image of the CCD sensor 15 is illustrated. As illustrated in the whole image of the CCD sensor 15, the CCD sensor 15 includes a CCD 15a, which is an imaging device, and a group 15b of filters. The group 15b of filters includes a multiplicity of filters B+Nb, filters G+Ng and filters R+Nr. In the right side of FIG. 5, a partially enlarged view of the group 15b of filters is illustrated. On the imaging surface (plane) of the CCD 15a, three kinds of color filters, namely, filters B+Nb, filters G+Ng and filters R+Nr, are formed. The filter B+Nb, the filter G+Ng or the filter R+Nr is formed on each pixel. These three kinds of color filters function as a spectral device (spectroscopic device). In FIG. 4A, the spectral transmittance (transmissivity) of each of the three kinds of color filters is illustrated. In FIG. 4B, only the spectral transmittance of the filter B+Nb is illustrated to more clearly illustrate the spectral transmittance. As illustrated in FIGS. 4A and 4B, the transmittance of each of these three color filters has a double-peak characteristic.

The filter B+Nb has a transmission characteristic of transmitting only B in the visible light region and only Nb in the near-infrared region, as illustrated with solid lines in FIG. 4A. The filter B+Nb functions as a spectral device for causing only B in the visible light region and only Nb in the near-infrared region to enter a pixel on which the filter is formed. Further, as illustrated with dotted lines in FIG. 4A, the filter G+Ng has a transmission characteristic of transmitting only G in the visible light region and only Ng in the near-infrared region. The filter G+Ng functions as a spectral device for causing only G in the visible light region and only Ng in the near-infrared region to enter a pixel on which the filter is formed. As illustrated with dash-dotted lines in FIG. 4A, a filter R+Nr has a transmission characteristic of transmitting only R in the visible light region and only Nr in the near-infrared region. The filter R+Nr functions as a spectral device for causing only R in the visible light region and only Nr in the near-infrared region to enter a pixel on which the filter is formed.

Therefore, the pixel on which the filter B+Nb is formed has sensitivity only to B in the visible light region and only to Nb in the near-infrared region. Further, the pixel on which the filter G+Ng is formed has sensitivity only to G in the visible light region and only to Ng in the near-infrared region. Further, the pixel on which the filter R+Nr is formed has sensitivity only to R in the visible light region and only to Nr in the near-infrared region. If the CCD sensor 15, which is structured as described above, is used, it is possible to obtain a spectral image of the image formed on the CCD sensor 15 not only in the visible light region but in the near-infrared region. Further, since a single filter has a band for transmitting light in the visible light region and a band for transmitting light in the near-infrared region, it is possible to obtain a spectral image in the visible light region and a spectral image in the near-infrared region by using the single imaging device for imaging.

Figure 6:
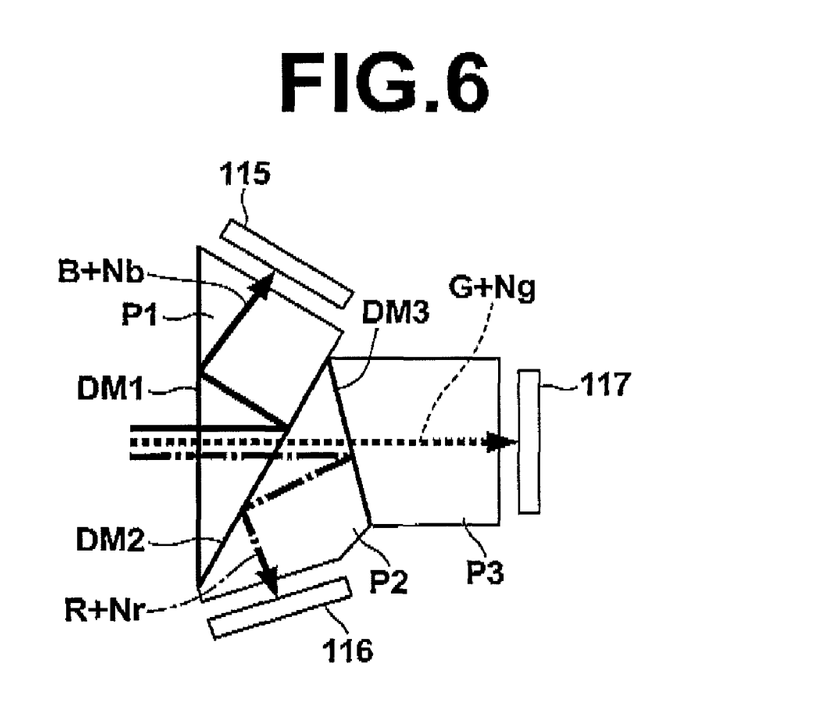
FIG. 6 is a diagram illustrating the structure of another example of the imaging unit.

Further, imaging units that are structured as illustrated in FIGS. 6 and 7 may be used instead of the CCD sensor 15, illustrated in FIG. 5. In the example illustrated in FIG. 6, a spectral device includes three prisms P1, P2 and P3. Further, dichroic coatings DM1, DM2 and DM3 are formed on the light incident surface of the prisms and the contact plane between the prisms. Accordingly, the incident light is divided into light including a light component B in the visible light region and a light component Nb in the near-infrared region, light including a light component G in the visible light region and a light component Ng in the near-infrared region, and light including a light component R in the visible light region and a light component Nr in the near-infrared region. Then, the three kinds of light are output to three directions. Further, CCD's 115, 116 and 117 are arranged for the three kinds of light that has been output to the three directions, respectively.

Figure 7A:
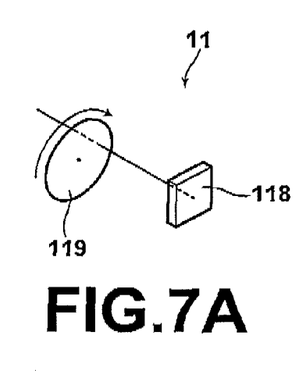
FIG. 7A is a diagram illustrating the structure of another example of the imaging unit.
Figure 7B:
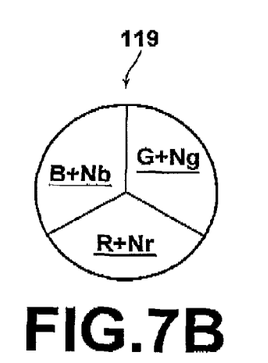
FIG. 7B is a diagram illustrating the structure of a spectral device.
Figure 7C:
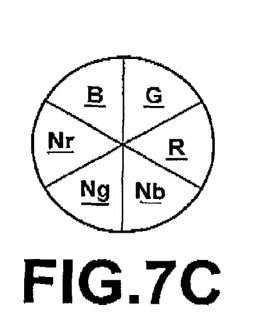
FIG. 7C is a diagram illustrating the structure of another spectral device.

The example illustrated in FIGS. 7A through 7C is a so-called switching type. As illustrated in FIG. 7A, a disk-shaped filter device 119 that is arranged in front of a CCD 118 is rotated with respect to the central axis. Accordingly, the wavelength band of light that enters the CCD 118 is switched. As illustrated in FIG. 7B, the disk-shaped filter device 119 is divided into three areas along the circumference direction. In the divided areas, a filter B+Nb, a filter G+Ng and a filter R+Nr, each functioning as a spectral device, are formed. Here, a filter device illustrated in FIG. 7C may be used instead of the filter device 119 illustrated in FIG. 7B. The filter device illustrated in FIG. 7C has a disk shape and the filter device is divided into six areas along the circumference direction. The six areas transmit light components B, G, R, Nb, Ng and Nr, respectively. If the filter device illustrated in FIG. 7C is used, an effect similar to the effect achieved by using the filter device 119 can be obtained.

In the example illustrated in FIG. 1, the CCD sensor 15 is provided in the scope 10. However, an image guide or the like for transmitting an image from the CCD sensor 15 may be inserted into the scope 10 and the CCD sensor 15 may be arranged in the outside of the scope 10. If the CCD sensor 15 is arranged in the outside of the scope 10, a spatial constraint within the scope 10 is eased. Therefore, the structure illustrated in FIG. 7A is more easily realized. Further, if this structure is adopted, the aforementioned structure, in which the white light source unit that outputs light including light that is not in the visible light region is used and a near-infrared light cut filter is removably provided in the optical path between the observation target 3 and the CCD, is more easily realized.

As illustrated in FIG. 1, a CCD drive circuit 16 for generating a drive pulse based on a synchronous signal is connected to the CCD sensor 15. Further, a CDS/AGC (correlated double sampling/automatic gain control) circuit 17 is connected to the CCD sensor 15. The CDS/AGC circuit 17 performs sampling on an image (video) signal output from the CCD sensor 15 and amplifies the signal. Further, an A/D (analog to digital) converter 18 for converting an analog output to a digital signal is connected to the CDS/AGC circuit 17. Further, a microcomputer 20 for controlling the aforementioned circuits and for controlling communication between the processor apparatus 12 and the scope 10 is provided in the scope 10.

Meanwhile, in the processor apparatus 12, a DSP (digital signal processor) 25 is provided. The DSP 25 performs various kinds of image processing on the image signal that has been digitized by the A/D converter 18. The DSP 25 generates a Y/C signal, which is composed of a luminance (Y) signal and chrominance (C) signals, from the image signal and outputs the Y/C signal.

In the apparatus according to the present embodiment, an ordinary image, a visible spectral image and a near-infrared spectral image are selectively formed (all of the images may be motion images (video images, motion pictures or the like) and still images (still pictures or the like)). Therefore, an end of a switch 26 for switching images to be formed among the aforementioned images is connected to the DSP 25. The DSP 25 may be arranged in the scope 10 instead of in the processor apparatus 12. An output terminal on the other end of the switch 26 can be selectively connected to a color signal processing circuit 38 for the ordinary image mode, a first color conversion circuit 28 for the visible spectral image mode and a first color conversion circuit 50 for the near-infrared spectral image mode.

First, the flow of processing in the visible spectral image mode will be described. The first color conversion circuit 28 converts the Y (luminescence)/C (chrominance) signal that has been output from the DSP 25 into three color image signals of R, G and B. On the downstream side of the first color conversion circuit 28, a color space conversion processing circuit 29, a number-of-colors selector 30, a second color conversion circuit 31, a signal processing circuit 32 and a D/A converter 33 are sequentially connected to each other in this order. The color space conversion processing circuit 29 performs a matrix operation for forming a spectral image and outputs image signals λ1$s$, λ2$s$ and λ3$s$ for forming spectral images for selected wavelength ranges λ1, λ2 and λ3. The number-of-colors selector 30 selects one of a single-color mode (monochrome mode) for forming a spectral image of a single narrow wavelength band and a three-color mode for forming a spectral image of three wavelength bands. The second color conversion circuit 31 receives the image signal λ1$s$, λ2$s$ or λ3$s$ in a single wavelength range as Rs, Gs or Bs signal or the image signals λ1$s$, λ2$s$ and λ3$s$ in three wavelength ranges as Rs, Gs and Bs signals so that processing corresponding to R, G and B signals is performed. Then, the second color conversion circuit 31 converts these signals into Y/C signals. The signal processing circuit 32 performs various kinds of signal processing, such as mirror image processing, mask generation and character generation. The D/A converter 33 at the end is connected to a monitor 34, such as a liquid crystal display or CRT, which is arranged in the outside of the processor apparatus 12, for example. Further, a two-color mode for forming a spectral image including two wavelength bands may be selected instead of the three-color mode selected by the number-of-colors selector 30. Here, the color space conversion processing circuit 29 functions as a spectral image formation circuit.

Meanwhile, the first color conversion circuit 50 for the near-infrared spectral image mode converts the Y (luminescence)/C (chrominance) signal that has been output from the DSP 25 into three color image signals of Nr, Ng and Nb. On the downstream side of the first color conversion circuit 50, a color space conversion processing circuit 51 is connected thereto. The color space conversion processing circuit 51 performs a matrix operation for forming a spectral image and outputs image signals λ1$s$', λ2$s$' and λ3$s$' for forming spectral images for wavelength ranges λ1', λ2' and λ3' that have been selected in the near-infrared region. Further, the color space conversion processing circuit 51 is connected to the aforementioned number-of-colors selector 30. Here, the color space conversion processing circuit 51 functions as the spectral image formation circuit of the present invention.

In FIG. 1, the first color conversion circuit 28 and the first color conversion circuit 50 are illustrated as different circuits from each other so that the difference in the modes is clearly illustrated. Further, the color space conversion processing circuit 29 and the color space conversion processing circuit 51 are illustrated as different circuits from each other so that the difference in the modes is clearly illustrated. However, the first color conversion circuit 28 and the first color conversion circuit 50 may be the same circuit. Further, the color space conversion processing circuit 29 and the color space conversion processing circuit 51 may be the same circuit.

Further, a microcomputer 35 is provided within the processor apparatus 12. The microcomputer 35 has a function for communicating with the scope 10. Further, the microcomputer 35 has a function for controlling each circuit and the light source unit 14 in the processor apparatus 12, a function for inputting matrix (coefficient) data for forming a spectral image to the color space conversion processing circuit 29 and the like. Further, a memory 36 is connected to the microcomputer 35. In the memory 36, matrix data that is used as predetermined coefficients to form a spectral image based on the R, G and B signals or based on the Nr, Ng and Nb signals is stored in the form of a table.

The matrix data for forming the spectral image based on the R, G and B signals may be calculated by using the method disclosed in Japanese Unexamined Patent Publication No. 2003-093336. Further, in the present embodiment, the matrix data for forming the spectral image based on Nr, Ng and Nb signals may be calculated by using, as a priori information, the spectral characteristic of the fluorescent agent with which the observation target 3 has been marked, instead of by using the spectral characteristic of illumination light. The spectral characteristic of illumination light is used to form a spectral image based on R, G and B signals.

Table 1 shows an example of matrix data for forming a spectral image based on R, G and B signals. The matrix data in Table 1 includes coefficients $k_r(\lambda)$, $k_g(\lambda)$ and $k_b(\lambda)$ ($\lambda$ represents a wavelength, which is dealt as a variable in Table 1) for matrix operation. The coefficients are set for each of 61 wavelength ranges, into which the wavelength range of 400 nm to 700 nm has been divided at intervals of 5 nm, for example.

TABLE 1

| WAVELENGTH($\lambda$) RANGE | $k_r(\lambda)$ | $k_g(\lambda)$ | $k_b(\lambda)$ |
|---|---|---|---|
| 400~404 | 0.000083 | −0.00188 | 0.003592 |
| . | . | . | . |
| . | . | . | . |
| . | . | . | . |
| 485~489 | −0.00115 | 0.000569 | 0.003325 |
| 490~494 | −0.00118 | 0.001149 | 0.002771 |
| 495~499 | −0.00118 | 0.001731 | 0.0022 |
| 500~504 | −0.00119 | 0.002346 | 0.0016 |
| 505~509 | −0.00119 | 0.00298 | 0.000983 |
| 510~514 | −0.00119 | 0.003633 | 0.000352 |
| . | . | . | . |
| . | . | . | . |
| . | . | . | . |
| 610~614 | 0.003236 | 0.001377 | −0.00159 |
| 615~619 | 0.003656 | 0.000671 | −0.00126 |
| 620~624 | 0.004022 | 0.000068 | −0.00097 |
| 625~629 | 0.004342 | −0.00046 | −0.00073 |
| 630~634 | 0.00459 | −0.00088 | −0.00051 |
| 635~639 | 0.004779 | −0.00121 | −0.00034 |
| 640~644 | 0.004922 | −0.00148 | −0.00018 |
| 645~649 | 0.005048 | −0.00172 | −0.000036 |
| 650~654 | 0.005152 | −0.00192 | 0.000088 |
| 655~659 | 0.005215 | −0.00207 | 0.000217 |
| . | . | . | . |
| . | . | . | . |
| . | . | . | . |
| 696~700 | 0.00548 | −0.00229 | 0.00453 |

Then, in the color space conversion processing circuit 29, matrix operation expressed by the following equation (1) is performed by using the coefficients $k_r(\lambda)$, $k_g(\lambda)$ and $k_b(\lambda)$ and the R, G and B signals output from the first color conversion circuit 28. Accordingly, the spectral image signals $\lambda 1s$, $\lambda 2s$ and $\lambda 3s$ are formed.

$$\begin{bmatrix} \lambda 1s \\ \lambda 2s \\ \lambda 3s \end{bmatrix} = \begin{bmatrix} k_r(\lambda 1) & k_g(\lambda 1) & k_b(\lambda 1) \\ k_r(\lambda 2) & k_g(\lambda 2) & k_b(\lambda 2) \\ k_r(\lambda 3) & k_g(\lambda 3) & k_b(\lambda 3) \end{bmatrix} \times \begin{bmatrix} R \\ G \\ B \end{bmatrix} \quad (1)$$

For example, if 500 nm, 620 nm and 650 nm are selected as the wavelength ranges $\lambda 1$, $\lambda 2$ and $\lambda 3$ that constitute a visible spectral image, matrix operation expressed by the following equation (2) is performed. The operation is performed, based on the above equation (1), by using, as the coefficients ($k_r$, $k_g$ and $k_b$), the coefficients (−0.00119, 0.002346 and 0.0016) corresponding to the center wavelength of 500 nm, the coefficients (0.004022, 0.000068 and −0.00097) corresponding to the center wavelength of 620 nm and the coefficients (0.005152, −0.00192 and 0.000088) corresponding to the center wavelength of 650 nm from 61 parameters in Table 1. The parameters may be read out from the memory 36 based on combinations of wavelengths stored in the memory 36.

$$\begin{bmatrix} \lambda 1s \\ \lambda 2s \\ \lambda 3s \end{bmatrix} = \begin{bmatrix} -0.00119 & 0.002346 & 0.0016 \\ 0.004022 & 0.000068 & -0.00097 \\ 0.005152 & -0.00192 & 0.000088 \end{bmatrix} \times \begin{bmatrix} R \\ G \\ B \end{bmatrix} \quad (2)$$

Further, when a spectral image based on Nr, Ng and Nb signals is formed, processing may be performed in a similar manner. Matrix operation expressed by the following equation (3) is performed by using coefficients $k_r'(\lambda)$, $k_g'(\lambda)$ and $k_b'(\lambda)$, which are stored for the near-infrared spectral image mode, and the Nr, Ng and Nb signals output from the first color conversion circuit 50. Accordingly, the spectral image signals $\lambda 1s'$, $\lambda 2s'$ and $\lambda 3s'$ are formed.

$$\begin{bmatrix} \lambda 1s' \\ \lambda 2s' \\ \lambda 3s' \end{bmatrix} = \begin{bmatrix} k_r'(\lambda 1) & k_g'(\lambda 1) & k_b'(\lambda 1) \\ k_r'(\lambda 2) & k_g'(\lambda 2) & k_b'(\lambda 2) \\ k_r'(\lambda 3) & k_g'(\lambda 3) & k_b'(\lambda 3) \end{bmatrix} \times \begin{bmatrix} N_r \\ N_g \\ N_b \end{bmatrix} \quad (3)$$

The other output terminal of the switch 26, illustrated in FIG. 1, is connected to the color signal processing circuit 38 for forming an ordinary color image, which is not a spectral image. The color signal processing circuit 38 is connected to a D/A (digital to analog) converter 39.

Figure 8:
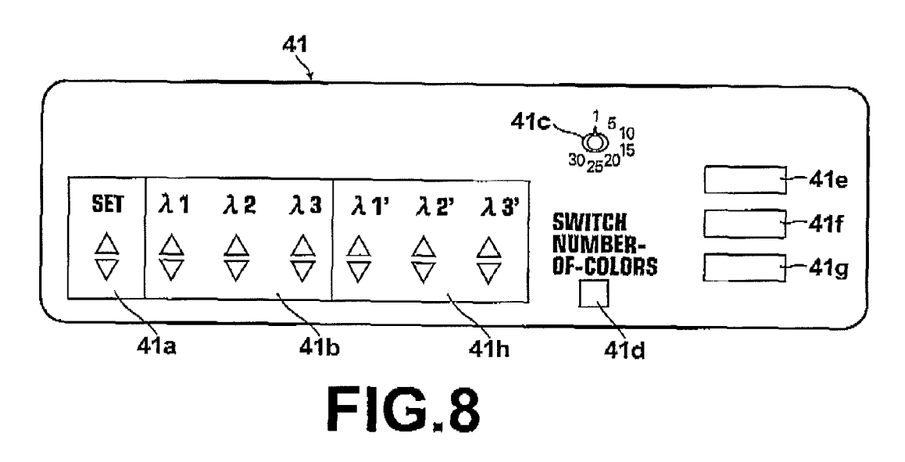
FIG. 8 is a diagram illustrating the structure of an operation panel.

The microcomputer 35 is connected to the memory 36, an operation panel 41 and an input unit 43 that includes a keyboard or the like. FIG. 8 is a diagram illustrating the operation panel 41 in detail. The operation panel 41 includes a wavelength set selection switch 41a, wavelength selection switches 41b and 41h, a switching-width setting switch 41c and a number-of-colors changing switch 41d. The wavelength set selection switch 41a is used to select a wavelength set of wavelength ranges $\lambda 1$, $\lambda 2$ and $\lambda 3$ that have been set in advance to form a spectral image. The wavelength selection switch 41b is used to select an arbitrary center wavelength for each of wavelength ranges $\lambda 1$, $\lambda 2$ and $\lambda 3$ to form a visible spectral image. The wavelength selection switch 41h is used to select an arbitrary center wavelength for each of wavelength ranges $\lambda 1'$, $\lambda 2'$ and $\lambda 3'$ to form a near-infrared spectral image. The switching-width setting switch 41c is used to set the width of change in the wavelength that is changed by the wavelength selection switches 41b and 41h.

Wavelength ranges $\lambda 1$, $\lambda 2$, $\lambda 3$, $\lambda 1'$, $\lambda 2'$ and $\lambda 3'$ that can be selected by using the wavelength set selection switch 41a, and which have been set in advance, may be the light emission wavelengths of fluorescent agents that can mark blood vessels, for example. Alternatively, the wavelength ranges may be the light emission wavelengths of fluorescent agents that can mark the blood vessels and the light emission wavelength of autofluorescence. Alternatively, the wavelength ranges may be the light emission wavelengths of different kinds of fluorescent agents that can mark cancer tissue or the like, for example. Such wavelength sets are stored, as default wavelength sets, in the memory 36, illustrated in FIG. 1.

The number-of-colors changing switch 41d is used to switch the modes between a single color mode (monochrome mode), which selects a single wavelength, and a three color mode. If the number-of-colors changing switch 41d is pressed during operation in the three color mode, the three color mode is switched to the single color mode. Then, the microcomputer 35 sets all of the wavelength ranges λ1, λ2 and λ3 to the same value, such as 650, for example. When the wavelength ranges λ1, λ2 and λ3 are set to the same value, an arbitrary value maybe selected by using the wavelength selection switches 41b and 41h.

Further, the operation panel 41 includes a visible spectral image formation switch 41e, a near-infrared spectral image formation switch 41f and an ordinary image display switch 41g. The visible spectral image formation switch 41e is used to form and display a spectral image in the visible light region. The near-infrared spectral image formation switch 41f is used to form and display a spectral image in the near-infrared region. The ordinary image display switch 41g is used to form and display an ordinary image. The visible spectral image form at ion switch 41e and the near-infrared spectral image formation switch 41f may be provided in the scope 10 instead of in the processor apparatus 12.

Here, some of the functions of the switches on the operation panel 41 may be replaced by key functions of the keyboard. Alternatively, all the functions of the switches may be replaced by the key functions of the keyboard.

Next, an operation of the electronic endoscope according to the present embodiment, which is structured as described above, will be described. First, an operation in the ordinary image mode will be described. In the ordinary image mode, white light is output from the light source unit 14 that is controlled by the microcomputer 35 and the observation target 3 is illuminated with the white light. As illustrated in FIG. 1, in the scope 10, the CCD sensor 15 is driven by the CCD drive circuit 16 and images the observation target. Then, the CCD sensor 15 outputs an imaging signal. In the CDS/AGC circuit 17, the imaging signal is amplified by correlated double sampling and automatic gain control. Then, A/D conversion is performed on the imaging signal at the A/D converter 18. The imaging signal is input to the DSP 25 in the processor apparatus 12 as the digital signal.

The DSP 25 performs gamma processing on the signals output from the scope 10. Further, the DSP 25 performs color conversion processing on the signals obtained through color filters, namely, the filters B+Nb, the filters G+Ng and the filters R+Nr. Accordingly, a Y/C signal, composed of a luminance (Y) signal and chrominance (C) signals, is formed. Then, an output from the DSP 25 is provided to the color signal processing circuit 38 by the switch 26. Then, the color signal processing circuit 38 performs predetermined processing, such as mirror image processing, mask generation and character generation. After the predetermined processing is performed by the color signal processing circuit 38, the D/A converter 39 converts the digital signal into an analog signal. Then, the analog signal is provided to the monitor 34, illustrated in FIG. 1. Accordingly, an ordinary color image of the observation target is displayed on the monitor 34.

Next, an operation in the visible spectral image mode will be described. When the visible spectral image formation switch 41e on the operation panel 41, illustrated in FIG. 8, is pressed, formation of a visible spectral image is instructed, and the mode is set to the visible spectral image mode. In the operation in the visible spectral image mode, processing till outputting a signal from the DSP 25 is similar to the processing in the ordinary image mode, as described above. After then, the switch 26 is switched to a state for providing the Y/C signal output from the DSP 25 to the first color conversion circuit 28. The first color conversion circuit 28 converts the Y/C signal into R, G and B signals. Further, the R, G and B signals are provided to the color space conversion processing circuit 29. The color space conversion processing circuit 29 performs matrix operation by using the equation (1) for forming a visible spectral image. The matrix operation is performed by using the R, G and B signals and matrix data. Specifically, in formation of the spectral image, three wavelength ranges λ1, λ2 and λ3 are set by operating the wavelength set selection switch 41a or the wavelength selection switch 41b on the operation panel 41. Further, the microcomputer 35 reads out matrix data corresponding to these three wavelength ranges from the memory 36 and inputs the matrix data to the color space conversion processing circuit 29.

If the three color mode has been selected by the number-of-colors selector 30, the spectral image signals λ1s, λ2s and λ3s are input to the second color conversion circuit 31, as three color image signals Rs, Gs and Bs, respectively. If the single color mode has been selected, one of the spectral image signals λ1s, λ2s and λ3s is input to the second color conversion circuit 31, as a color image signal Rs, Gs or Bs. The second color conversion circuit 31 converts the three color image signals Rs, Gs and Bs into a Y/C signal (Y, Rs-Y, Bs-Y). Then, the Y/C signal is input to the aforementioned monitor 34 or the like through the signal processing circuit 32 and the D/A converter 33.

Next, an operation in the near-infrared spectral image mode will be described. When the near-infrared spectral image formation switch 41f on the operation panel 41, illustrated in FIG. 8, is pressed, formation of a near-infrared spectral image is instructed, and the mode is set to the near-infrared spectral image mode. In the operation in the near-infrared spectral image mode, excitation light is output from the light source unit 14 by being controlled by the microcomputer 35 and the observation target 3 is illuminated with the excitation light. The fluorescent agent with which the observation target 3 has been marked is excited and fluoresce is output. In the light sent from the observation target 3, the excitation light reflected from the observation target 3 is blocked by the excitation cut filter 9 and only the fluorescence is transmitted through the excitation cut filter 9.

As illustrated in FIG. 1, in the scope 10, the CCD sensor 15 is driven by the CCD drive circuit 16 and images the observation target. Then, the CCD sensor 15 outputs an imaging signal. The CDS/AGC circuit 17 amplifies the imaging signal by performing correlated double sampling and automatic gain control. Further, the A/D converter 18 performs A/D conversion on the amplified signal and the digital signal is input to the DSP 25 in the processor apparatus 12.

The DSP 25 performs gamma processing on the signals output from the scope 10. Further, the DSP 25 performs color conversion processing on the signals obtained through color filters, namely, the filters B+Nb, the filters G+Ng and the filters R+Nr. Accordingly, a Y/C signal, composed of a luminance (Y) signal and chrominance (C) signals, is formed.

After then, the switch 26 is switched to a state for providing the Y/C signal output from the DSP 25 to the first color conversion circuit 50. The first color conversion circuit 50 converts the Y/C signal into Nr, Ng and Nb signals. The Nr, Ng and Nb signals are provided to the color space conversion processing circuit 51. The color space conversion processing circuit 51 performs the aforementioned matrix operation to form a near-infrared spectral image. The matrix operation is performed by using the Nr, Ng and Nb signals and matrix data. Specifically, in formation of the spectral image, three wavelength ranges λ1', λ2' and λ3' are set by operating the wavelength set selection switch 41a or the wavelength selection switch 41h on the operation panel 41. Further, the microcomputer 35 reads out matrix data corresponding to the three selected wavelength ranges from the memory 36 and inputs the matrix data to the color space conversion processing circuit 51.

If the light emission wavelength of the fluorescent agent with which the observation target 3 has been marked is selected as the wavelength $\lambda 1'$, $\lambda 2'$ or $\lambda 3'$, it is possible to obtain a sharper (clearer) image, extracting a region dyed with the fluorescent agent.

Further, in this mode, if the three color mode has been selected by the number-of-colors selector 30, the spectral image signals $\lambda 1s'$, $\lambda 2s'$ and $\lambda 3s'$ are input to the second color conversion circuit 31, as three color image signals Rs, Gs and Bs, respectively. If the single color mode has been selected, one of the spectral image signals $\lambda 1s'$, $\lambda 2s'$ and $\lambda 3s'$ is input to the second color conversion circuit 31, as a color image signal Rs, Gs or Bs. The second color conversion circuit 31 converts the three color image signals Rs, Gs and Bs into a Y/C signal (Y, Rs-Y, Bs-Y). Then, the Y/C signal is input to the aforementioned monitor 34 or the like through the signal processing circuit 32 and the D/A converter 33.

Figure 9:
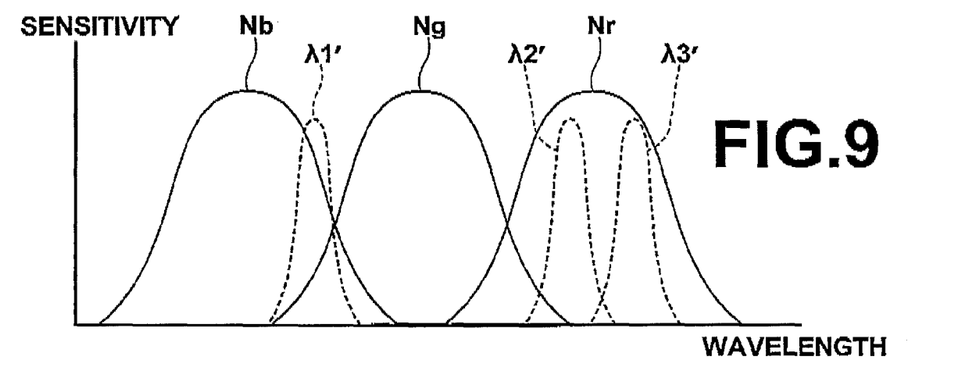
FIG. 9 is a diagram illustrating an example the wavelength range of a spectral image and the spectral sensitivity characteristic of the spectral device.

The spectral image displayed on the monitor 34 as described above is composed of color components in the wavelengths illustrated in FIG. 9, for example. Specifically, FIG. 9 is a conceptual diagram in which the spectral sensitivity characteristics Nr, Ng and Nb of the color filters in the near-infrared region are superposed on three wavelength ranges $\lambda 1'$, $\lambda 2'$ and $\lambda 3'$ for forming the spectral image. The spectral image signals $\lambda 1s'$, $\lambda 2s'$ and $\lambda 3s'$ are color signals in wavelength ranges, each having a range of approximately $\pm 10$ n. A spectral image (a motion image and a still image) composed of a combination of colors in these three wavelength ranges is displayed.

The operation panel 41 includes the visible spectral image formation switch 41e, the near-infrared spectral image formation switch 41f and the ordinary image display switch 41g. The visible spectral image, the near-infrared spectral image and the ordinary image can be displayed by operating the respective switches. Further, at least two arbitrary images of these images may be displayed at the same time. If the images are displayed in such a manner, it is possible to observe an ordinary image for general observation and a spectral image in which a predetermined target has been unblurred and to compare them with each other. Further, it is possible to display at least two arbitrary images of the visible spectral image, the near-infrared spectral image and the ordinary image in such a manner that they are superimposed one on another. Accordingly, it becomes possible to clearly recognize the region marked with the fluorescent agent.

Further, in the aforementioned embodiment, a case in which the observation target 3 is marked with the three kinds of fluorescent agents and a region dyed with the fluorescent agents is extracted has been described. However, the wavelength of fluorescence that is used to form the spectral image is not limited to the wavelength of fluorescence induced from the outside of the organism. For example, as described below, the wavelength of autofluorescence in the organism may be used.

Currently, a technique for recognizing the accurate positions of blood vessels by intravenously administering a fluorescent agent, such as ICG, is used. This technique is used to recognize the accurate positions of the blood vessels in real-time during surgery so that the surgery is smoothly performed. Further, the technique is used to prevent undesirable bleeding during and after the surgery by performing necessary procedures during the surgery.

In that case, if an artifact, such as autofluorescence from a fluorescence emitting body (tissue or cells) other than the blood vessels that have been dyed with the fluorescent agent, is present, it is impossible to recognize the accurate positions of the blood vessels. Therefore, for example, the light emission wavelength of ICG and the light emission wavelength of the autofluorescence are selected as the wavelengths for forming the spectral images. Then, it becomes possible to extract the blood vessels and the autofluorescence emitting body. Further, a sharp image of the blood vessels can be obtained by performing image processing so that the autofluorescence emitting body is not displayed. Specifically, the aforementioned spectral technique can reduce the adverse effect of the artifact. Further, it becomes possible to stably obtain sharp and clear images of the blood vessels.

There is increasing need for accurate recognition of the positions of the blood vessels, as described above, not only in endoscopic surgeries (endoscopy) but particularly in laparoscopic surgeries (laparoscopy). In recent years, the number of surgeries by laparoscopy is increasing because the laparoscopy generally requires a shorter period of hospitalization than laparotomy. The shorter period of hospitalization can reduce the medical expenses. Further, the laparoscopy can reduce the burden on the patients. In the laparoscopy, unlike the ordinary laparotomy, a surgeon can not check the position of tissue by palpation. Therefore, the surgeon needs to rely on images of the blood vessels to recognize the positions of the blood vessels. If the blood vessels are damaged during the surgery, bleeding occurs, which causes a damage to the patient. Therefore, the surgeon has a strong desire to quickly recognize the positions of the blood vessels during the surgery.

Generally, in the endoscopic surgery, blood vessels that have diameters of approximately 0.5 mm are observed within the depth of approximately 2 mm. Meanwhile, in the laparoscopy, blood vessels that have diameters in the range of approximately 2.5 to 6 mm that are present in the fatty layer at the depth of approximately 10 mm are observed. Therefore, in the laparoscopy, it is necessary to recognize the positions of the blood vessels that are situated at a relatively deep position. In this respect, a fluorescent image obtained by using light in a near-infrared region (700 to 1300 nm) is useful because the light in the near-infrared region does not attenuate much in the organism.

Fluorescence emitted from a deep position is diffused by tissue and a blur is generated. Therefore, when an image of blood vessels at the deep position is obtained, it is desirable to perform image processing on the image to obtain a sharper image. For example, the image processing technique disclosed in Japanese Unexamined Patent Publication No. 10(1998)-165365 maybe used. In this technique, a blur of the image caused by scattering of light in the organism is estimated based on simulation using a priori information about the tissue and the point spread function of an image that is actually obtained. Then, restoring processing is performed by image processing, thereby obtaining a sharper image of the blood vessels.

Figure 10A:
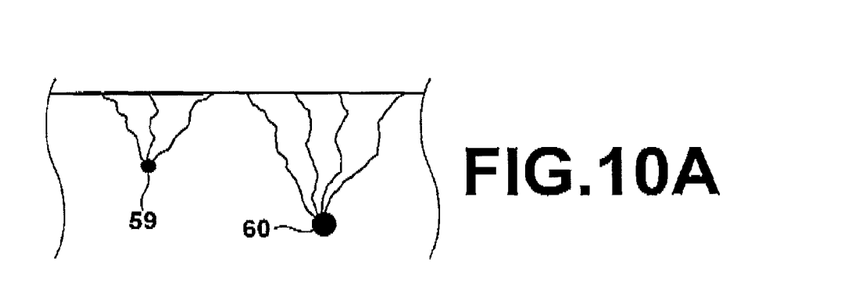
FIG. 10A is a diagram illustrating the section of blood vessels in tissue.
Figure 10B:
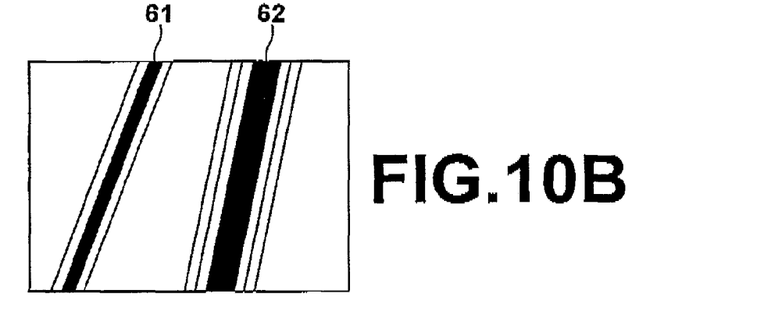
FIG. 10B is a schematic diagram illustrating a blurred image of blood vessels.
Figure 10C:
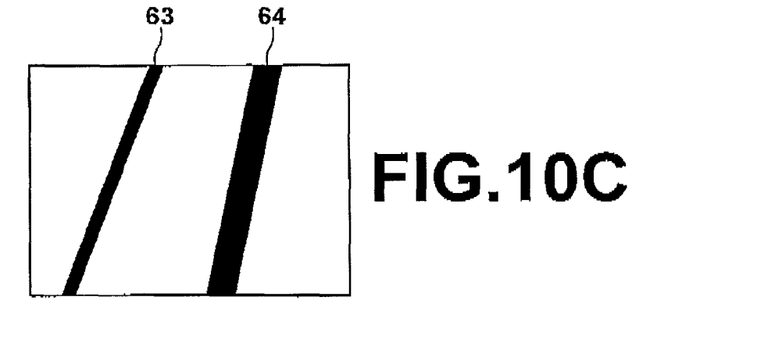
FIG. 10C is a schematic diagram illustrating an image of the blood vessels after image processing.

An example of this processing method will be outlined with reference to FIGS. 10A, 10B and 10C. FIG. 10A is a sectional view illustrating two blood vessels 59 and 60, which are present at different depths from each other in the tissue. When images of the blood vessels that are present at deep positions of the tissue as illustrated in FIG. 10A are obtained, blurred images 61 and 62 are obtained, as schematically illustrated in FIG. 10B. In these blurred images 61 and 62, the depths are estimated based on the degrees of blurs in the peripheral portions of the blood vessels with respect to the central portions thereof. Then, sharp images 63 and 64 of the blood vessels, as illustrated in FIG. 10C, can be obtained by restoring the images by using a blur function obtained by simulation.

Figure 11:
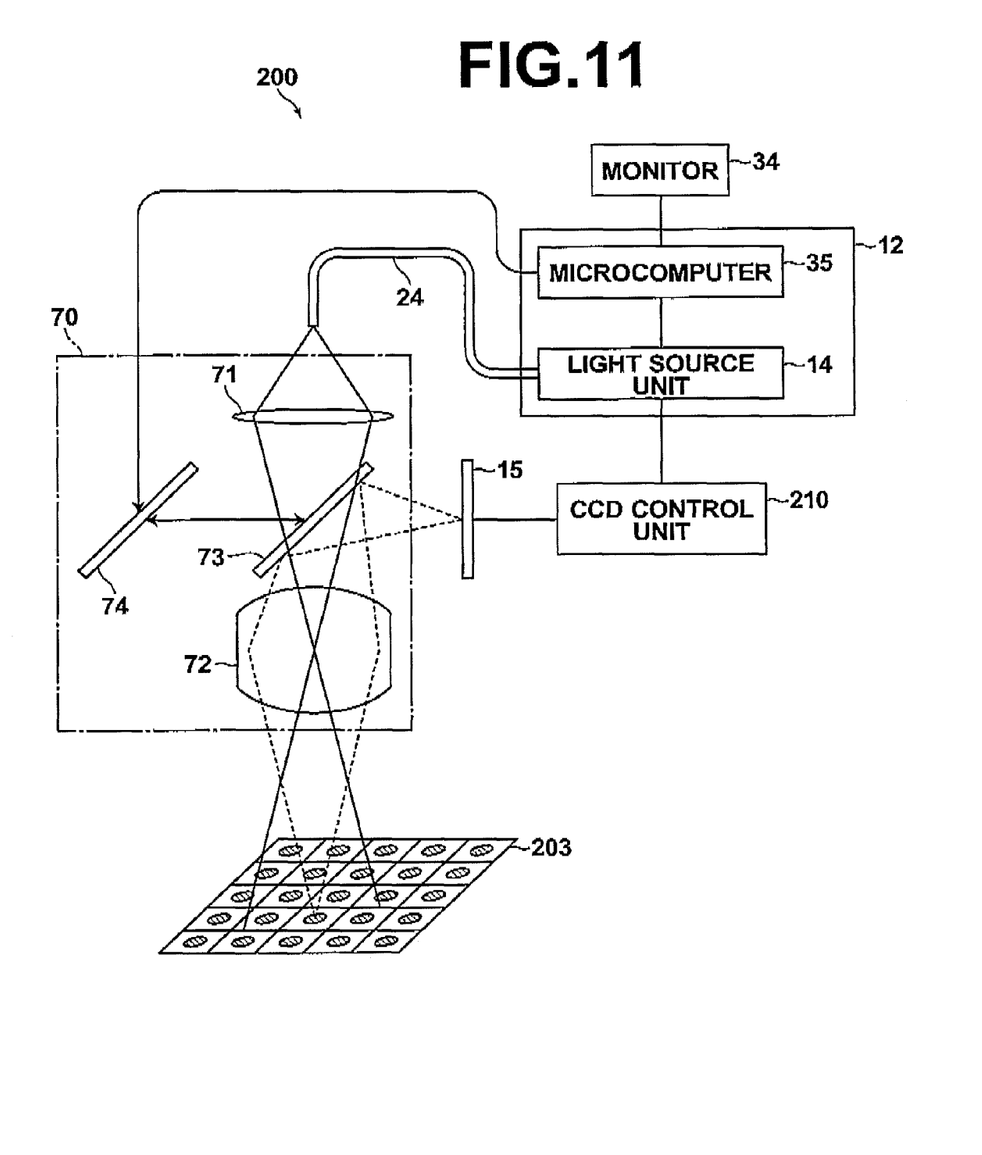
FIG. 11 is a schematic diagram illustrating the configuration of an examination apparatus according to a second embodiment of the present invention.

Next, an imaging apparatus according to a second embodiment of the present invention will be described with reference to FIG. 11. FIG. 11 is a schematic diagram illustrating the configuration of an examination apparatus 200 as the imaging apparatus according to the second embodiment of the present invention. In the present embodiment, a multiplicity of slices of living organism tissue that have been dyed with fluorescent agent or agents are used as an observation target 203 (an object 203 to be observed). The multiplicity of slices are two-dimensionally arranged. The examination apparatus 200 obtains a fluorescence image of the observation target 203, as specimens, and performs diagnosis based on the obtained fluorescence image. Further, the examination apparatus 200 operates in the ordinary image mode, the near-infrared spectral image mode and the visible spectral image mode in a manner similar to the operation of the electronic endoscope apparatus 100 in the first embodiment.

As illustrated in FIG. 11, the examination apparatus 200 includes the light source unit 14, the light guide 24, an optical system 70, the CCD sensor 15, a CCD control unit 210 and the processor apparatus 12. The light source unit 14 outputs light and the light guide 24 transmits the light output from the light source unit 14. The optical system 70 illuminates the observation target 203 with the light transmitted through the light guide 24 and forms an image of the observation target 203. The CCD sensor 15 images the observation target 203 that has been formed by the optical system 70. The CCD control unit 210 is connected to the CCD sensor 15. The processor apparatus 12 performs processing such as operation processing. In the examination apparatus 200, the light source unit 14, the CCD sensor 15 and the processor apparatus 12 have the functions and structures similar to those of the first embodiment. Therefore, the explanation of these units will be omitted. Further, in FIG. 11, only the light source unit 14 and the microcomputer 35 are illustrated as the elements of the processor apparatus 12, and other elements are omitted.

The optical system 70 basically includes a condensing lens 71, an imaging lens (image formation lens) 72, a dichroic mirror 73 and a half mirror 74. The condensing lens 71 condenses light output from the light guide 24. The imaging lens 72 forms an image of the observation target 203 on the CCD sensor 15. The dichroic mirror 73 is removably arranged in the optical path between the condensing lens 71 and the imaging lens 72. The half mirror 74 and the dichroic mirror 73 are interchangeable.

In the near-infrared spectral image mode, the dichroic mirror 73 is inserted to the optical path and inclined at 45 degrees with respect to the optical axis of the imaging lens 72. In the ordinary image mode and in the visible spectral image mode, the dichroic mirror 73 is removed from the optical path. When the dichroic mirror 73 is arranged as described above, the dichroic mirror 73 passes the excitation light from the light guide 24 and blocks the excitation light reflected from the observation target 203. Further, the dichroic mirror 73 reflects the fluorescence from the observation target 203.

The half mirror 74 transmits approximately 50% of incident light regardless of the wavelength of the light and reflects the remaining light, which is approximately 50% of the incident light. In the ordinary image mode and in the visible spectral image mode, the dichroic mirror 73 is inserted to the optical path and inclined at 45 degrees with respect to the optical axis of the imaging lens 72. In the near-infrared spectral image mode, the half mirror 74 is removed from the optical path.

The condensing lens 71 condenses light output from the light guide 24. The condensing lens 71 is set so that the light is condensed at a position other than the observation target 203. Optionally, the condensing position of the light by the condensing lens 71 may be set at the pupil position of the imaging lens 72. It is desirable that the optical system is structured in such a manner that after the light that has been output from the light guide 24 is transmitted through the condensing lens 71 and the imaging lens 72, the light is divergent light or parallel light. If the optical system is structured in such a manner, it is possible to reduce the unevenness in illumination on the observation target 203.

The CCD sensor 15 is structured in a manner similar to the first embodiment illustrated in FIGS. 4A and 5. The CCD sensor 15 is arranged in the optical path of light reflected by the dichroic mirror 73 or the half mirror 74. The CCD sensor 15 is arranged at the image formation position of the observation target 203 by the imaging lens 72.

The CCD controller 210 is connected to the CCD sensor 15. The CCD controller 210 includes the CCD drive circuit 16, the CDS/AGC (correlated double sampling/automatic gain control) circuit 17, the A/D converter 18 and the microcomputer 20 of the elements included in the scope 10 of the first embodiment. Further, the processor apparatus 12 that has a structure similar to the first embodiment is connected to the downstream side of the CCD control unit 210. An image formed by the CCD sensor 15 is displayed on the monitor 34.

Next, the operation of the examination apparatus 200 according to the present embodiment will be described. In the near-infrared spectral image mode, the microcomputer 35 makes the light source unit 14 output excitation light. Then, the excitation light output from the light guide 24 is transmitted through the dichroic mirror 73 and the imaging lens 71 and illuminates the whole observation target 203. A fluorescent agent contained in the observation target 203 emits fluorescence by being illuminated with the excitation light and a fluorescent image of the observation target 203 is formed on the CCD sensor 15 by the imaging lens 72. Then, the CCD sensor 15 images the image formed thereon. The excitation light that has been reflected from the observation target 203 is blocked by the dichroic mirror 73. Therefore, the reflected light does not reach the CCD sensor 15. After the CCD sensor 15, the processing and image formation similar to the processing in the first embodiment or the like is performed. Then, a near-infrared spectral image is displayed on the monitor 34.

In the ordinary image mode and the visible spectral image mode, the microcomputer 35 makes the light source unit 14 output white light. The white light is output from the light guide 24 and transmitted through the half mirror 74. Then, the white light is transmitted through the imaging lens 72 and illuminates the observation target 203. Light reflected from the observation target 203 is transmitted through the imaging lens 72 and an image of the observation target 203 is formed on the CCD sensor 15 by the imaging lens 72. Then, the CCD sensor 15 images the image formed thereon. After the CCD sensor 15, the processing and image formation similar to the processing in the first embodiment or the like is performed. Then, an ordinary image or a visible spectral image is displayed on the monitor 34.

The examination apparatus 200, as described above, may be used for ex vivo diagnosis during a surgery of a cancer, for example. Specifically, a specimen, such as a lymph node, obtained during the surgery is marked with a plurality of kinds of fluorescent agents that can mark cancer tissue. Then, presence of a metastasis of the cancer to the lymph node is detected by observing a fluorescent image of the specimen. Accordingly, the metastasis of the cancer to the lymph node can be diagnosed.

In current surgeries of cancers, all of cancer cells and suspicious regions surrounding the cancer cells are excised in many cases to prevent recurrence and metastasis of the cancers. Therefore, the patients tend to suffer from pains or the like after the surgeries. For example, in the case of breast cancers, some patients suffer from restricted movement of their arms, swelling (lymphedema) or the like after the surgeries.

Conventionally, as a method for preventing the aforementioned excision or total extirpation, a lymph node or the like in the vicinity of the cancer tissue is excised during the surgery, as ex vivo diagnosis. Then, pathologic diagnosis is performed by producing a frozen slice of the lymph node or the like. However, since this method requires an extremely high technique, the method is not widely used. Further, it is desirable that a larger number of slices are observed to improve the accuracy of diagnosis. However, since the pathologic diagnosis is performed during the surgery, time for diagnosis is limited. Further, only a part of the lymph node or a single section (sectional plane) of the lymph node can be observed instead of the whole lymph node, because the thickness of the specimen is approximately 40 µm. Therefore, in the conventional method, there is a risk that cancer is overlooked.

However, in the examination apparatus 200 according to the embodiment of the present invention, to which diagnosis using fluorescence is applied, light in a wavelength range that has high transmittance with respect the living organism is used. Therefore, a thicker slice may be used as the specimen. For example, even if a specimen has a thickness of approximately 2 mm, a fluorescent image of the specimen can be obtained. Therefore, it is possible to suppress an increase in the number of specimens. Further, it is possible to diagnose the presence of a metastasis of the cancer with respect to the whole extracted lymph nodes. Hence, the risk of overlooking the metastasis is significantly reduced. Further, since the metastasis to the lymph nodes is quickly diagnosed, it is possible to accurately determine a region to be excised. Further, if a diagnostic standard is defined at the examination apparatus 200, it is possible to perform quick and accurate diagnoses by using a standardized diagnostic method.

Further, in diagnosis of cancers by marking cancer tissue with a fluorescent antibody, the antibody does not always combine with the cancer tissue at 100%. Therefore, it is desirable that a plurality of kinds of fluorescent substances are used to improve the accuracy of diagnoses. In the examination apparatus 200, a plurality of kinds of fluorescence can be separately detected by setting a plurality of selection wavelengths for obtaining spectral images. Therefore, it is possible to improve the accuracy of diagnoses. Further, if a judgment standard of diagnosis is set for each of the plurality of fluorescent agents, the accuracy of diagnosis can be further improved.

So far, preferred embodiments of the present invention have been described with reference to the attached drawings. However, the present invention is not limited to the aforementioned examples. For example, in the above embodiment, a case using a primary-color-type RGB color filter was described. However, a supplementary-color-type filter (Mg (magenta), Ye (yellow), Cy (cyan) and G (green)) may be used instead of the primary-color-type RGB color filter.

Further, in the above embodiments, cases in which spectral images are formed by using image signals of three colors, such as R, G and B signals or Nr, Ng and Nb signals, in other words, by using image signals based on three light components in different wavelength ranges were described, as examples. However, in the present invention, the number of the image signals used to form the spectral images is not limited to three as in the above embodiments. The spectral images may be formed by using image signals based on at least two light components in different wavelength ranges from each other.

Further, in the above embodiments, cases in which spectral images are formed by selecting three wavelengths, were mainly described as examples. However, the number of the wavelengths selected at the time of forming the spectral images is not limited to three as in the above embodiments. The number of the wavelengths selected may be one or two or four or even greater than four.

Figure 12:
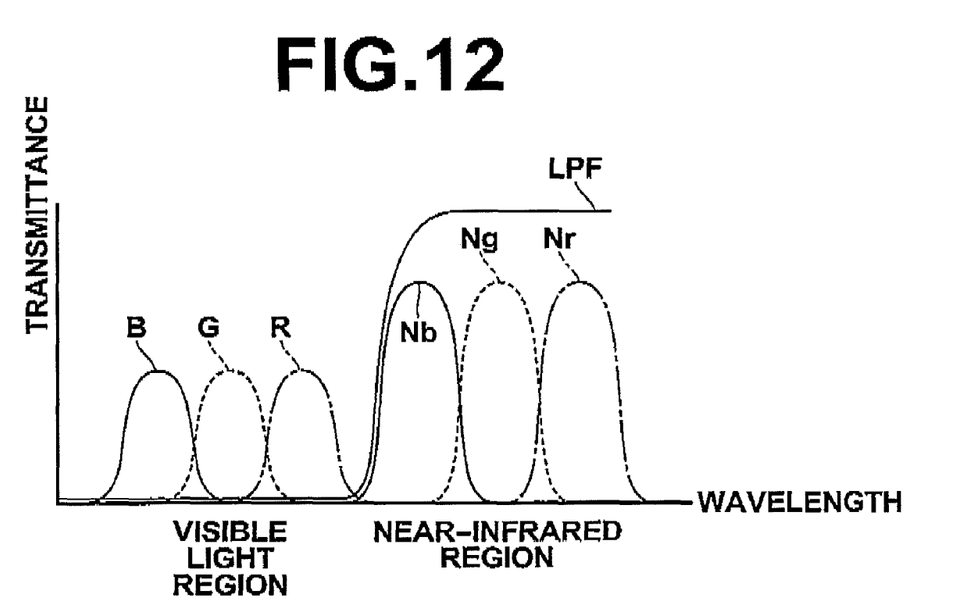
FIG. 12 is a diagram illustrating the spectral transmission characteristic of a long-pass filter and the spectral transmission characteristics of color filters.

Further, in the above embodiments, the white light source unit was used in the ordinary image mode and the visible spectral image mode. However, the white light source unit may be used in all of the ordinary image mode, the visible spectral image mode and the near-infrared mode. Then, a long pass filter that has a transmission characteristic illustrated as "LPF" in FIG. 12 may be removably provided in the optical path between the observation target and the CCD. The long pass filter may be removed from the optical path in the ordinary image mode and in the visible spectral image mode and the long pass filter may be inserted into the optical path in the near-infrared spectral image mode. Accordingly, the white light source unit may be used in all of the modes. The LPF illustrated in FIG. 12 shows the transmission characteristic that light in a visible region is cut and light in a near-infrared region is transmitted. The LPF can be used when the wavelength of the excitation light is in the visible region.

Further, in the above embodiments, cases in which the imaging apparatus of the present invention is embodied as the electronic endoscopic apparatus and the examination apparatus were described as examples. However, the present invention is not limited to these apparatuses and may be applied to other kinds of apparatuses, such as an analysis apparatus.

Further, in the above embodiments, the spectral image mode has both of the visible spectral image mode and the near-infrared spectral image mode. However, in the present invention, it is not necessary that the spectral image mode has the visible spectral image mode. The present invention may have a structure in which the visible spectral image mode is omitted.

Further, in the above embodiments, the ordinary image, the spectral image in the visible light region and the spectral image in the near-infrared region are formed and displayed by pressing the switches. However, the present invention is not limited to the above embodiments. A display method in which the three kinds of images are automatically displayed as motion images in an alternate manner may be adopted. Alternatively, a display method in which the ordinary image and the spectral image in the near-infrared region are automatically displayed as motion images in an alternate manner may be adopted. Further, the apparatus may be structured so that a display method may be selected from these display methods or the like.

Further, the examination apparatus 200 in the second embodiment forms the ordinary image, the spectral image in the visible light region and the spectral image in the near-infrared region. However, for example, if it is not necessary to form the original image and a user wishes to perform only detection of fluorescence, the examination apparatus 200 may have a simpler structure. Next, this example will be described as a modification example of the examination apparatus 200 in comparison with the examination apparatus 200.

In the modification example, it is not necessary to form the ordinary image. Therefore, the white light source unit may be omitted from the light source unit 14. Further, the half mirror 7 may be omitted. Further, as the color filter that is provided on the light receiving surface of the CCD sensor 15, a single-peak filter that does not have a transmission characteristic of R, G and B but only have a transmission characteristic of Nr, Ng and Nb may be used. This applies to the structures illustrated in FIGS. 6 and 7 in a similar manner. Specifically, a spectral device that does not have a transmission characteristic of R, G and B but only have a transmission characteristic of Nr, Ng and Nb may be used.

Further, in the first and second embodiments, the wavelength ranges of Nr, Ng and Nb are set in the near-infrared range because the ordinary image is formed. However, in the modification example, such restriction is not present. Therefore, the wavelength ranges corresponding to Nr, Ng and Nb during imaging and the wavelength ranges to be selected to form the spectral images may be set by selecting the ranges from a wider range of wavelengths. In that case, the wavelength ranges may be set by selecting ranges from the wavelength band of 600 to 1300 nm, which is appropriate for observation of living organisms.

What is claimed is:

1. An imaging apparatus comprising:

a light source unit that can selectively output white light and light in a wavelength band that is different from that of the white light to an observation target;

an imaging unit that includes an imaging device for imaging the observation target that is illuminated with the light output from the light source unit, the imaging device having first pixels and second pixels, and the imaging unit further including first spectral devices that make only first light components in a visible light region and fourth light components in a near-infrared region enter the first pixels of the imaging device and second spectral devices that make only second light components in the visible light region and fifth light components in the near-infrared region enter the second pixels of the imaging device, wherein the imaging unit selectively obtains an image of the observation target for each of the first light components, the second light components and third light components, which are three kinds of light components in different wavelength ranges from each other in the visible light region, and an image of the observation target for each of at least the fourth light components and the fifth light components, which are at least two kinds of light components in different wavelength ranges from each other in the near-infrared region; and a spectral image formation circuit that generates a spectral image signal representing a spectral image that has a specified wavelength by performing an operation using an image signal based on an output from the imaging unit and predetermined matrix data.

2. An imaging apparatus, as defined in claim 1, wherein the spectral image formation circuit generates the spectral image signal by using the image signal that is at least based on the fourth light components and the fifth light components.

3. An imaging apparatus, as defined in claim 1, wherein the specified wavelength is the wavelength of fluorescence, and wherein the light in the wavelength band that is different from that of the white light is excitation light for exciting the fluorescence.

4. An imaging apparatus, as defined in claim 1, wherein a color image based on the first light components, the second light components and the third light components in the visible light region, a first spectral image based on at least two of the first light components, the second light components and the third light components in the visible light region and a second spectral image based on at least the fourth light components and the fifth light components in the near-infrared region can be formed.

5. An imaging apparatus, as defined in claim 4, wherein at least two of the color image, the first spectral image and the second spectral image can be displayed at the same time.

6. An imaging apparatus, as defined in claim 4, wherein at least two of the color image, the first spectral image and the second spectral image can be displayed in such a manner that they are superimposed one on another.

* * * * *